(12) United States Patent
Lin

(10) Patent No.: US 7,686,278 B2
(45) Date of Patent: Mar. 30, 2010

(54) TOOTH MOLD RETAINING FRAME

(76) Inventor: Chao-Hung Lin, 235 Chung-Ho Box 8-24, Taipei (TW)

( * ) Notice: Subject to any disclaimer, the term of this patent is extended or adjusted under 35 U.S.C. 154(b) by 344 days.

(21) Appl. No.: 11/799,485

(22) Filed: May 2, 2007

(65) Prior Publication Data
US 2008/0272271 A1    Nov. 6, 2008

(51) Int. Cl.
*A61C 19/00* (2006.01)
(52) U.S. Cl. ............ 249/54; 425/451.5; 425/459; 433/50; 433/57; 433/61; 433/63
(58) Field of Classification Search ............ 249/54; 425/451, 451.5, 459; 433/49, 50, 53–54, 433/57–58, 61–67
See application file for complete search history.

(56) References Cited
U.S. PATENT DOCUMENTS
6,186,781 B1 * 2/2001 Iba ............... 433/50
6,634,883 B2 * 10/2003 Ranalli ............... 433/50

* cited by examiner

*Primary Examiner*—Yogendra Gupta
*Assistant Examiner*—Thu Khanh T Nguyen

(57) ABSTRACT

A tooth mold retaining frame comprises an L shape seat; a pivotal block; a universal connector; a first positioning block; a second positioning block; and a first fine adjust unit. By using the first fine adjust unit, second fine adjust unit and the fine-adjust device, an upper teeth mold, and a lower teeth mold can move with respect to one another precisely. By a universal connector, the upper teeth mold can move three directionally and can lift or descend proportionally so as to avoid the error in manufacturing of the teeth mold. Thus the teeth mold can be made precisely and the condition of the teeth mold can be viewed conveniently. Furthermore, the teeth mold can be sent directly without needing to send the teeth frame. Thus, the manufacturer can make the teeth mold continuously without affecting the working time.

7 Claims, 8 Drawing Sheets

TOOTH MOLD RETAINING FRAME

FIELD OF THE INVENTION

The present invention relates to teeth mold retaining frames, and particularly to a tooth mold retaining frame, wherein by a universal connector, the upper teeth mold can move three directionally and can lift or descend proportionally so as to avoid the error in manufacturing of the teeth mold. Thus the teeth mold can be made precisely and the condition of the teeth mold can be viewed conveniently. Furthermore, the teeth mold can be sent directly without needing to send the teeth frame. Thus, the manufacturer can make the teeth mold continuously without affecting the working time.

BACKGROUND OF THE INVENTION

Referring to FIG. 1, a prior art tooth mold retaining frame 90 is illustrated. A seat 91 is pivoted with an upper seat 92 at an upper end thereof. A lower end of the seat has a lower seat 93. The upper seat 92 has a positioning block 921 and the lower seat 93 has a positioning block 931. The positioning blocks 921, 931 have respective magnets. A shaped teeth mold T is absorbed between the upper seat and the lower seat. The upper seat 92 is pivotally rotated with respect to the seat 91 so as to view the engagement of the teeth of the teeth mold T. Moreover, a front end and a rear end of the upper seat 92 are installed with fine-adjust devices 94, 95 for controlling the height or opening of the teeth mold T so as to adjust the position of the teeth mold T so that the worker can adjust the engagement of the teeth.

Referring to FIG. 1A, in use of the tooth mold retaining frame 90, some limitation are required. For example, when an iron sheet B is placed on the magnet of the set, in current technology, in the initial stage, a rubber ring encloses the upper seat 92 or the lower seat 93. The gypsum is filled into a mold A as a teeth mold seat T1. Then a prepared teeth mold is placed thereon. After drying, the mold A is taken down so as to complete the teeth mold T. Then another symmetrical engaged teeth mold T2 is made and then complete the respective symmetrical teeth mold T'. However the teeth molds T and T' will have different compression ratios due to different solidifying states so that errors in biting are induced. The precision in the manufactured denture is not good. Each tooth mold retaining frame has errors in the manufacturing process. The teeth molds T and T' made by the same tooth mold retaining frame can not be used with another tooth mold retaining frame 90. Thus, the teeth molds T and T' and the tooth mold retaining frame must be sent to the dentist together for aligning in the engagement and communicates with the patient. However the tooth mold retaining frame can not be used to make another teeth mold during this time period.

SUMMARY OF THE INVENTION

Accordingly, the primary object of the present invention is to provide a tooth mold retaining frame, wherein by a universal connector, the upper teeth mold can move three directionally and can lift or descend proportionally so as to avoid the error in manufacturing of the teeth mold. Thus the teeth mold can be made precisely and the condition of the teeth mold can be viewed conveniently. Furthermore, the teeth mold can be sent directly without needing to send the teeth frame. Thus, the manufacturer can make the teeth mold continuously without affecting the working time.

To achieve above objects, the present invention provides a tooth mold retaining frame comprising: an L shape seat; two lateral sides of the L shape seat being extended from the button seat and a supporting frame being installed above the two lateral sides; each of two ends of the supporting frame having a retaining groove; a pivotal block having a pivotal rod and a connecting portion; two ends of the pivotal rod being secured to the two retaining grooves of the supporting frame; a universal connector; one end of the universal connector being connected to the connecting portion of the pivotal block; a first positioning block; a lower side of the first positioning block having a protrusion and at least one nose; the first positioning block being connected to the universal connector; the first positioning block being movable with respect to the universal connector; a second positioning block being positioned on the lower seat and having a protrusion and at least one nose; and a first fine adjust unit including a top plate and an adjust button; the top plate being connected to the pivotal block; the adjust button passing through the supporting frame and one end thereof resisting against the top plate so that the top plate moves longitudinally to drive the pivotal block, universal connector and the first positioning block; a fine-adjust device installed on the L shape seat by using an adjust screw to adjust the second positioning block to move leftwards or rightwards; and a second positioning block including a telescopic rod one end of which is installed to the L shape seat and another end of which resists against the pivotal block; the telescopic rod having an adjust button for adjusting a length of the telescopic rod so as to adjust the position of seat; wherein by using the first fine adjust unit, second fine adjust unit and the fine-adjust device, an upper teeth mold, and a lower teeth mold can move with respect to one another precisely.

The various objects and advantages of the present invention will be more readily understood from the following detailed description when read in conjunction with the appended drawing.

DETAILED DESCRIPTION OF THE INVENTION

Figure 1:
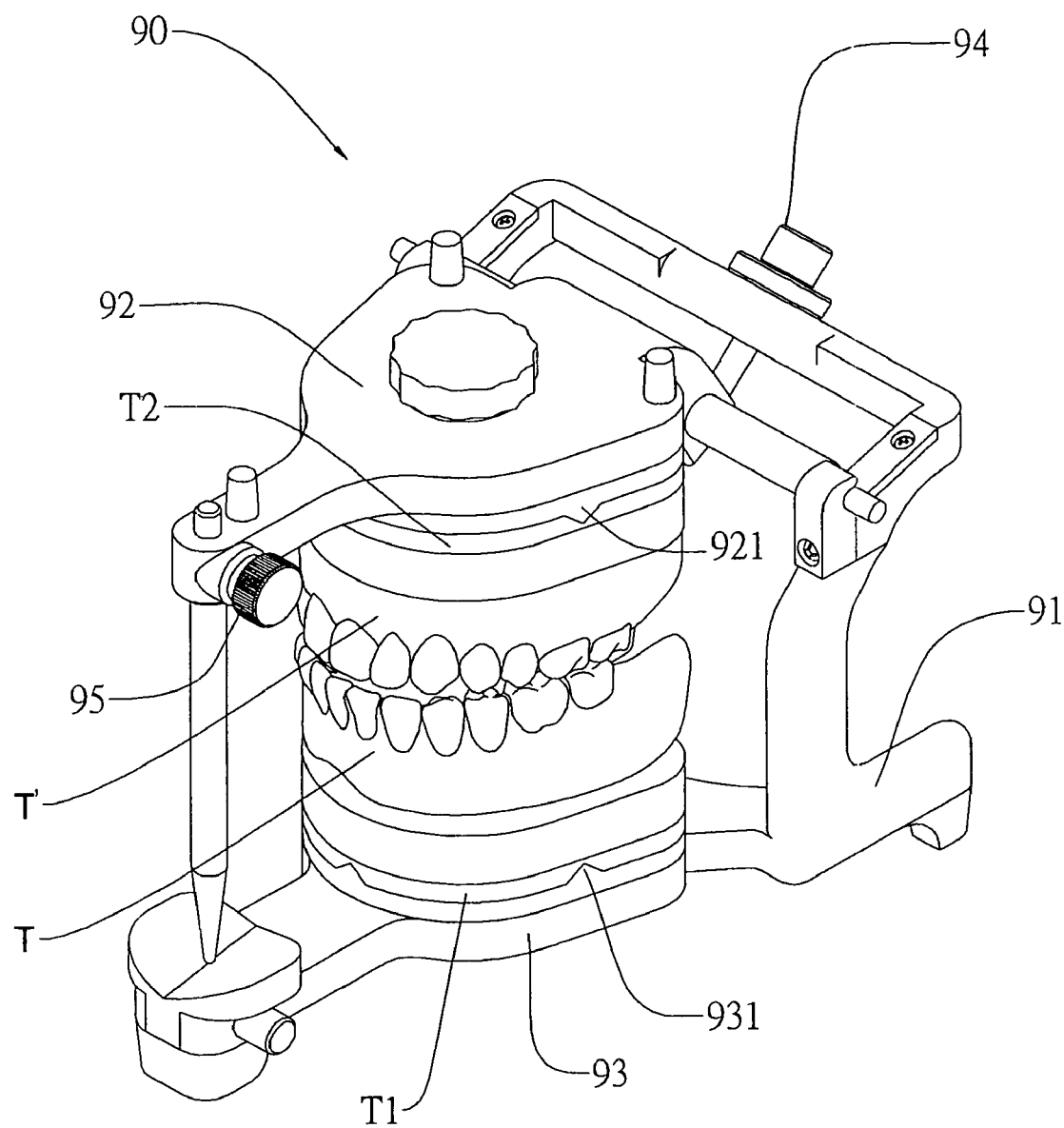
FIG. 1 is a perspective view of the prior art tooth frame.
Figure 1A:
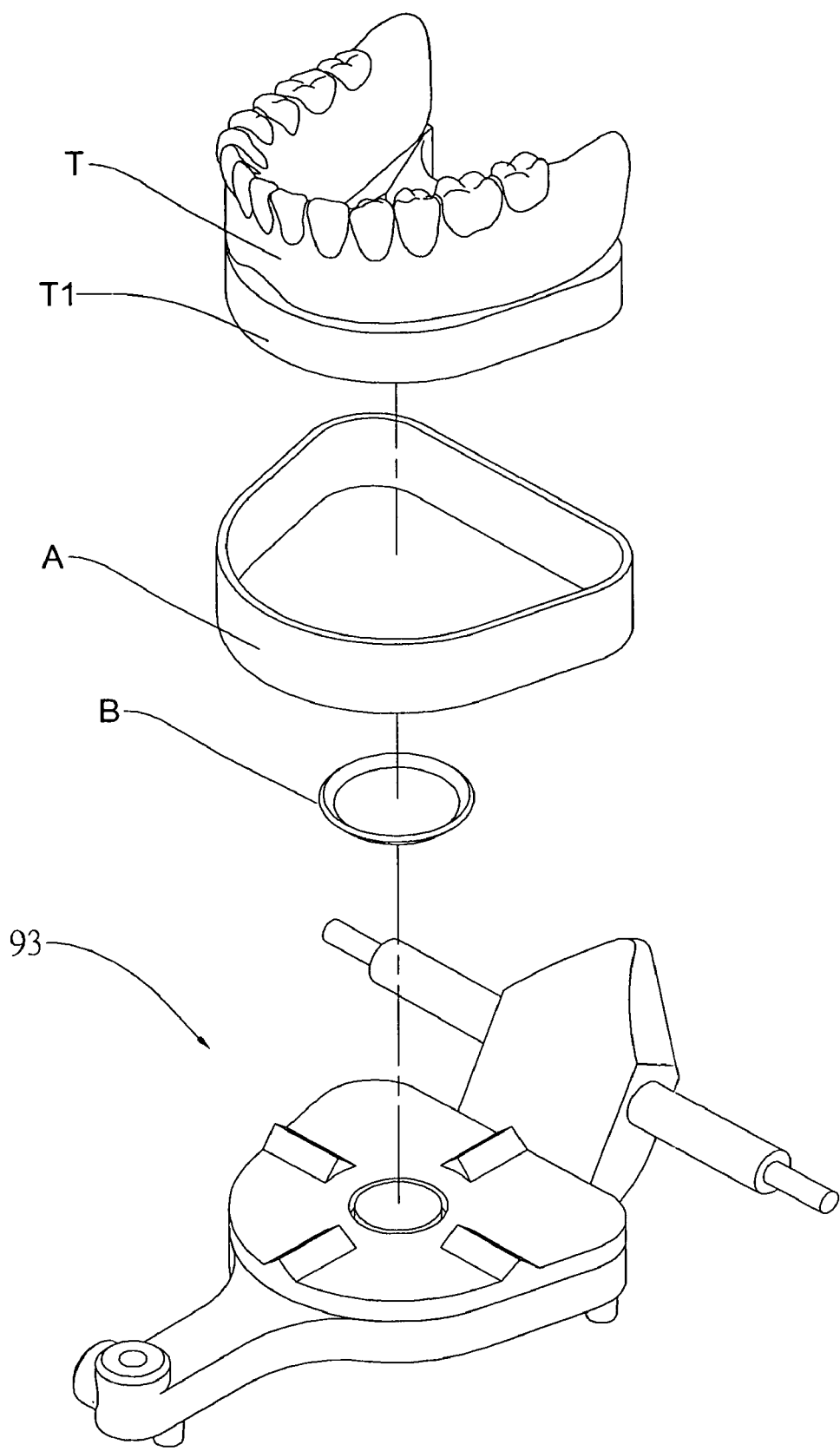
FIG. 1A is an exploded view of the teeth mold retainer.
Figure 2:
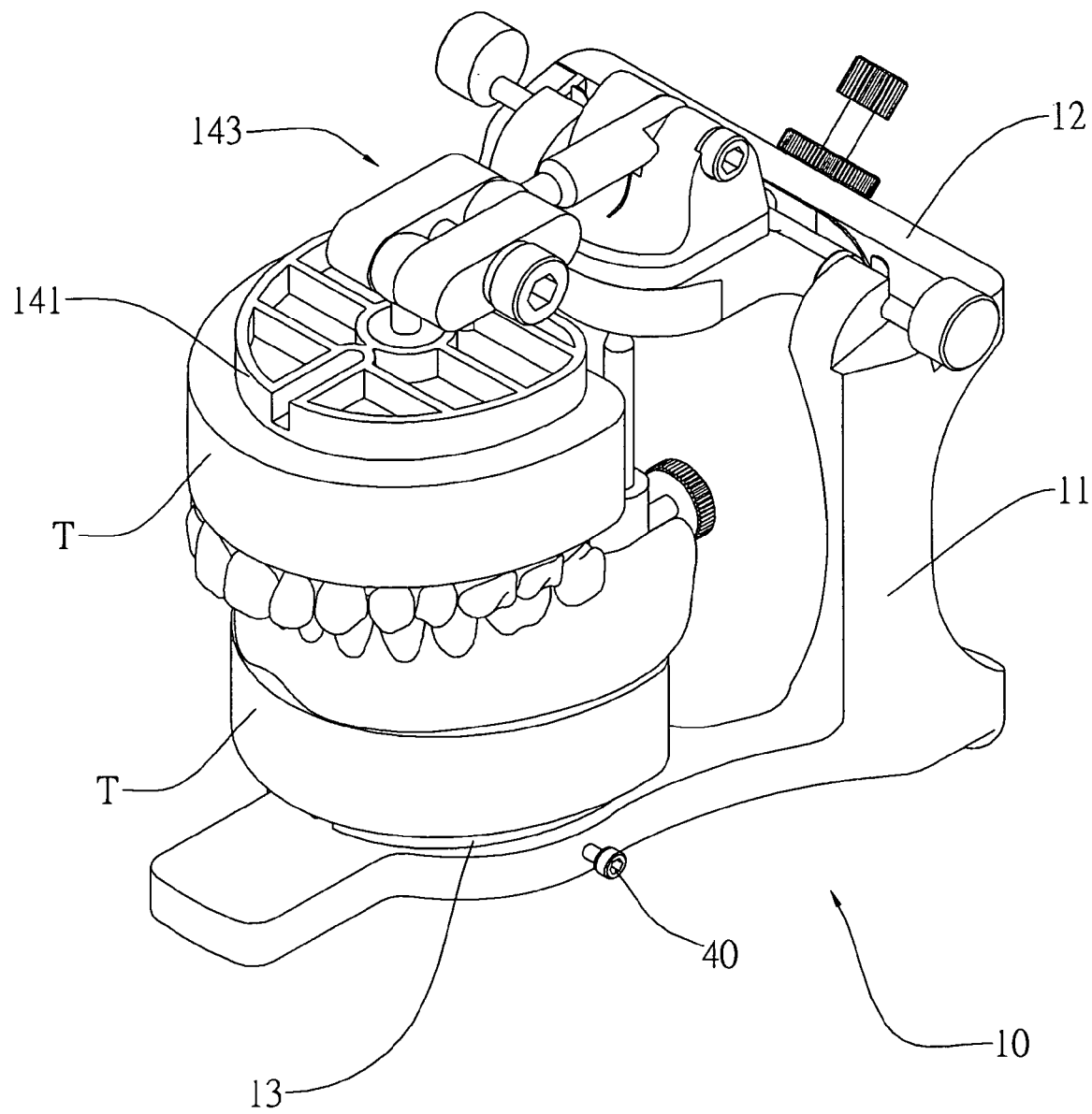
FIG. 2 is a perspective view of the embodiment of the present invention.
Figure 3:
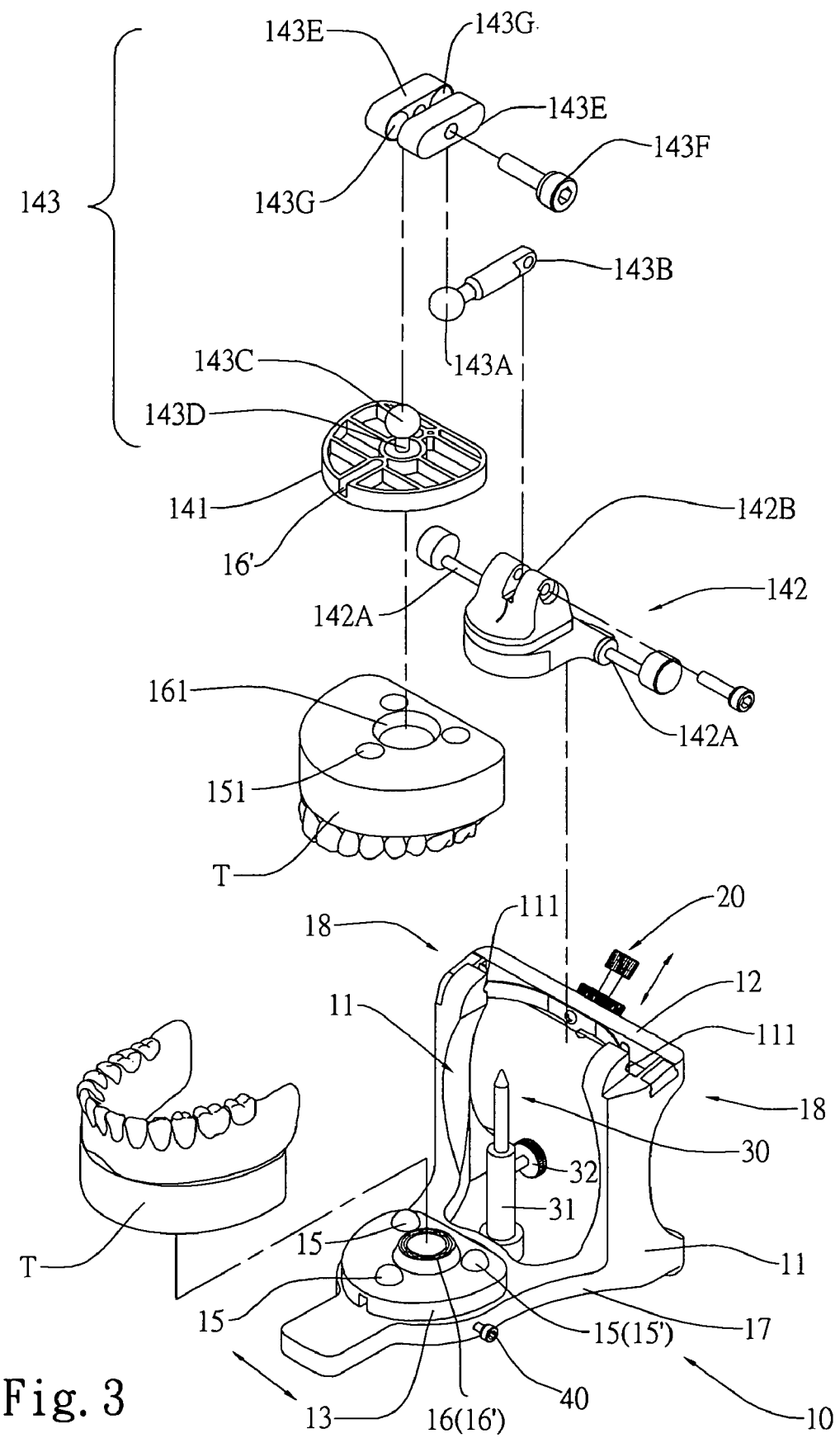
FIGS. 3 to 7 are schematic views showing the operations of the embodiment of the present invention.

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims. Referring to FIGS. 2 and 3, the structure of the present invention is illustrated. The present invention has the following elements.

An L shape seat 10 has a lower seat 17, a pivotal block 111, an universal connector 143, a first positioning block 141, a second positioning block 13, a first fine adjust unit 20, a second fine adjust unit 30, and a fine-adjust device 40. Two lateral sides 11 are extended from the button seat 17 and a supporting frame 12 is installed above the two lateral sides 11. Each of two ends of the supporting frame 12 has a retaining groove 111.

The pivotal block 142 has a pivotal rod 142A and a connecting portion 142B. Two ends of the pivotal rod 142A are secured to the two retaining grooves 111 of the supporting frame 12.

One end of the universal connector 143 is connected to the connecting portion 142B of the pivotal block 142.

A lower side of the first positioning block 141 has a protrusion 16' and at least one nose 15'. In this embodiment, there are three noses 15'. Preferably, the nose 15' has a tapered shape. A magnet (not shown) is installed within the protrusion 16'. The noses 15' and the protrusion 16' of the first positioning block 141 are identical to those in the second positioning block 13, but at the lower side of the first positioning block 141. The first positioning block 141 is connected to a universal connector 143. The first positioning block 141 is movable with respect to the universal connector 143.

In this embodiment, a teeth mold T is used, which has three positioning holes 151 and a recess portion 161. A metal sheet (not shown) attracted by the magnet is installed within the recess portion 161. The first positioning block 141 serves to combine and detach the teeth mold T and the pivotal block 142 quickly.

The second positioning block 13 is positioned on the lower seat 17 and has a protrusion 16 and at least one nose 15. The protrusion 16 is combined with a magnet therein (not shown).

Moreover, the universal connector 143 includes a first rod body 143B and a first ball valve 143A connected at an upper end of the first rod body 143B. The first ball valve 143A is pivoted to the connecting portion 142B of the pivotal block 142 so that the first rod body 143B and the pivotal block 142 are formed as a movably joint. The universal connector 143 further includes a second rod body 143D and a second ball valve 143C. One end of the second rod body 143B is connected to the second ball valve 143C. The second ball valve 143C is connected to the first positioning block 141 so that the first positioning block 141 and the universal connector 143 are movable with respect to the pivotal block 142 and are lifted with an equal ratio. Furthermore, universal connector 143 includes a clamping unit which includes two clamping blocks 143E and one adjust screw 143F. The adjust screw 143F passes through the two clamping blocks 143E so as to tighten or release the two clamping block 143E. Each clamping block 143E is formed with two recesses 143G at a side facing to another clamping block 143E for receiving the first ball valve 143A and the second ball valve 143C. When the adjust screw 143F is adjusted to make the two clamping blocks 143E move closer, the two ball valves will be compressed to as to has a great damping. On the contrary, when the gap between the two clamping blocks 143E is enlarged, the pressure applied to the ball valves will decreased so that the ball valves are rotatable. The universal connector 143 can move with respect to the pivotal block 142 so that the teeth mold T on the first positioning block 141 can move three directionally.

Further the first fine adjust unit 20 includes a top plate 21 and an adjust button 32. The top plate 21 is connected to the pivotal block 142. The adjust button 32 passes through the supporting frame 12 and one end thereof resists against the top plate 21 so that the top plate 21 moves longitudinally to drive the pivotal block 142, universal connector 143 and the first positioning block 141. The fine-adjust device 40 is installed on the L shape seat 10, by for example using an adjust screw 41 to adjust the second positioning block 13 to move leftwards or rightwards. Thus structure is known in the prior art and thus the detail will not be described herein. The second positioning block 13 includes a telescopic rod 41 one end of which is installed to the L shape seat 10 and another end of which resists against the pivotal block 142. The telescopic rod 31 has an adjust button 32 for adjusting a length of the telescopic rod 31 (referring to FIG. 3) so as to adjust the position of seat. Thus, by using the first fine adjust unit 20, second fine adjust unit 30 and the fine-adjust device 40, the upper teeth mold, and lower teeth mold T can move with respect to one another precisely.

Figure 4:
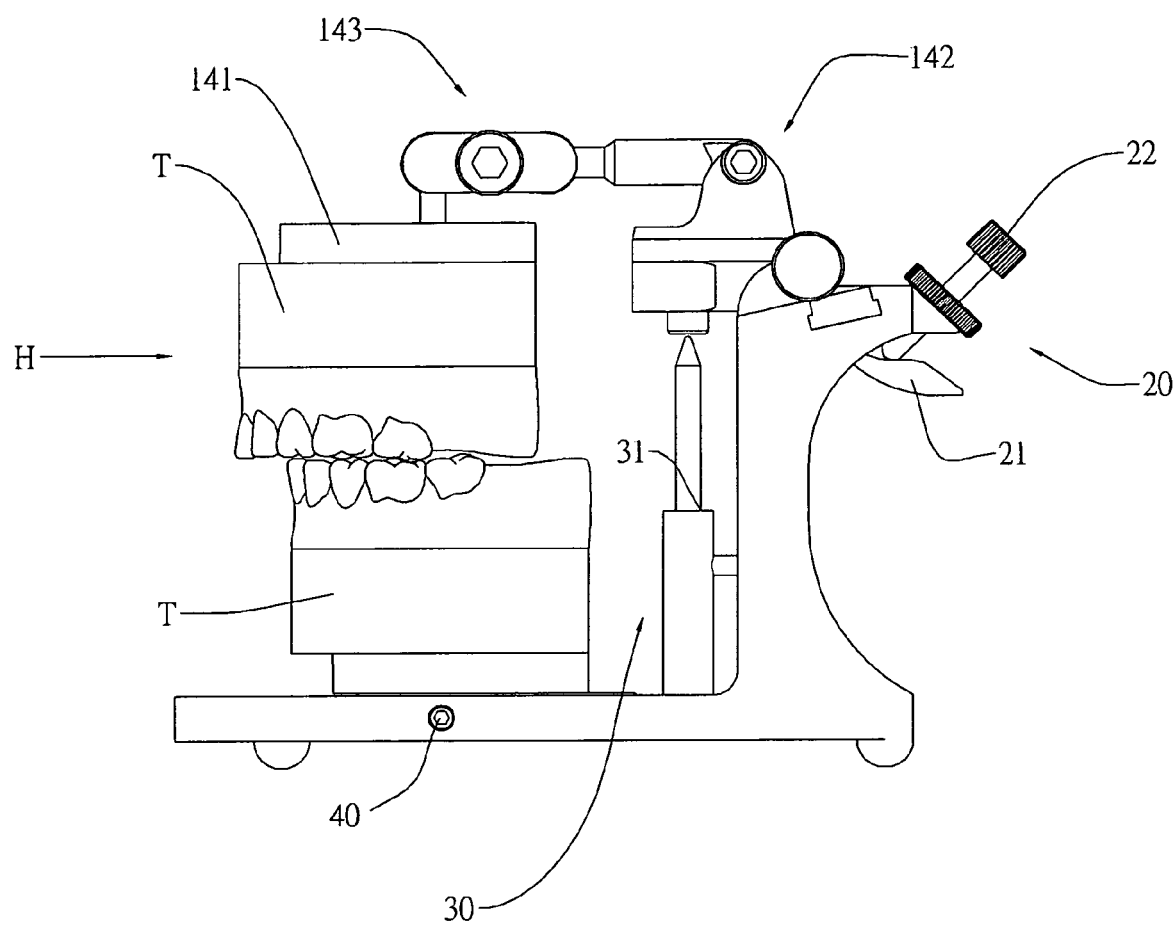
Figure 5:
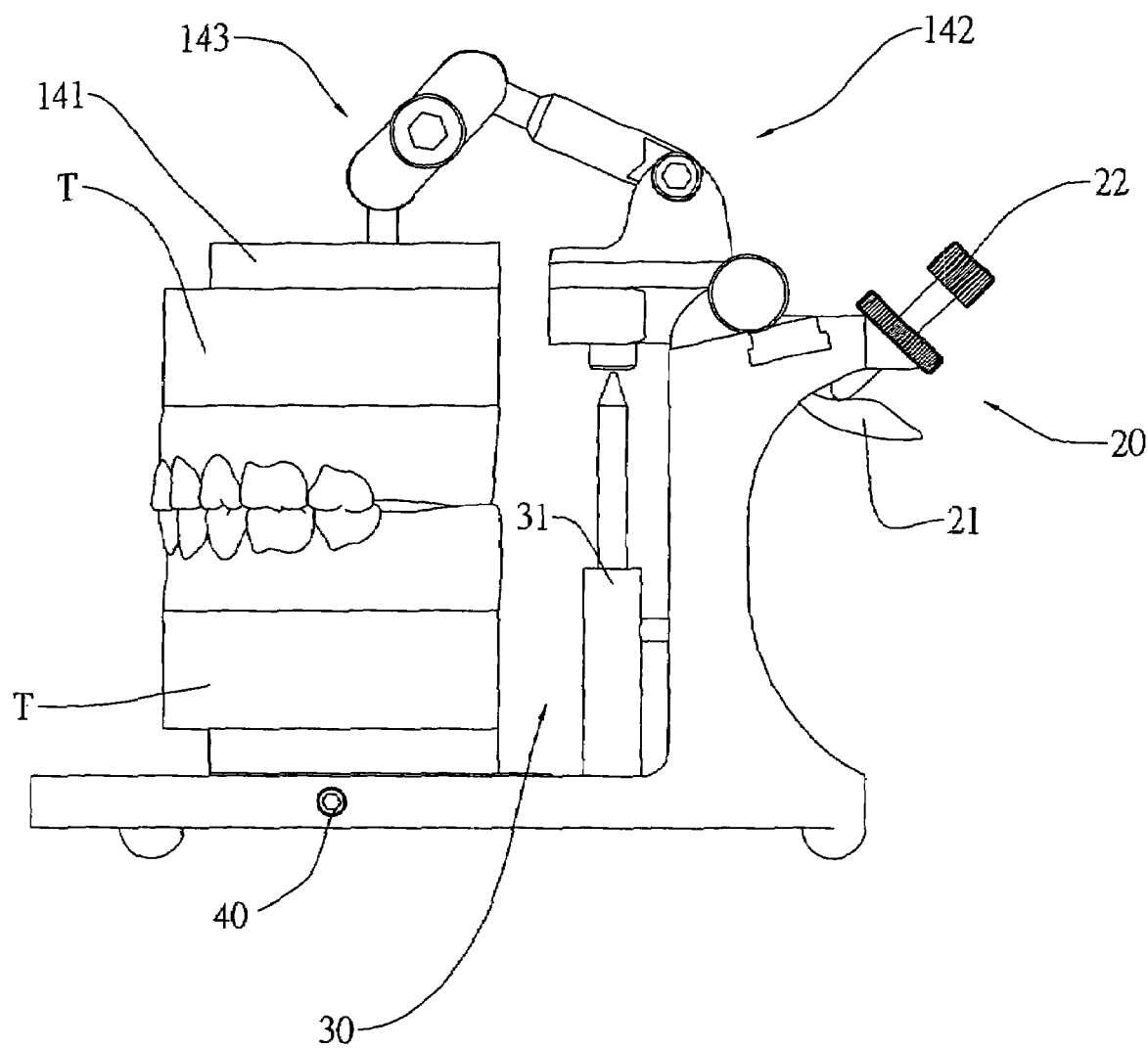
Figure 6:
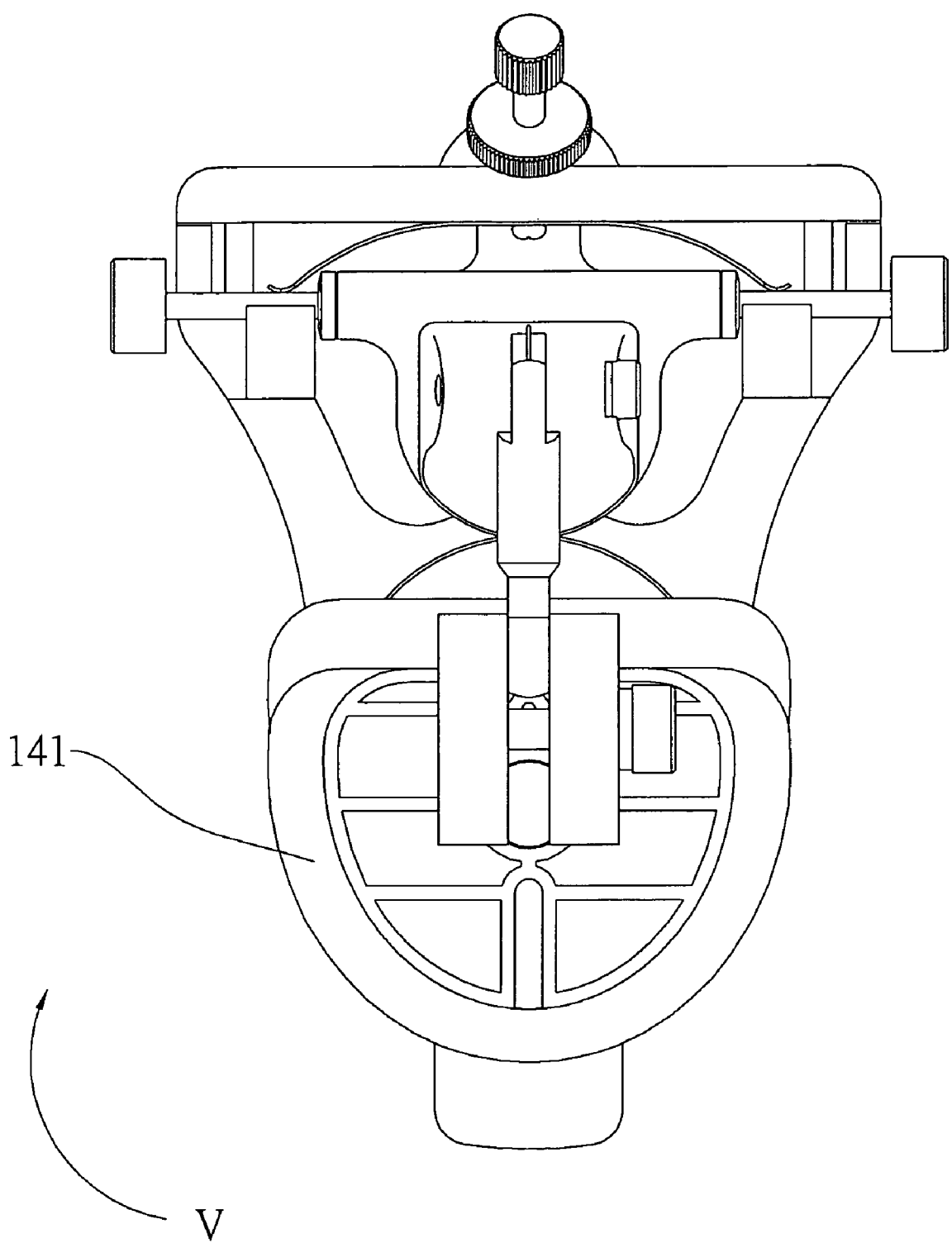
Figure 7:
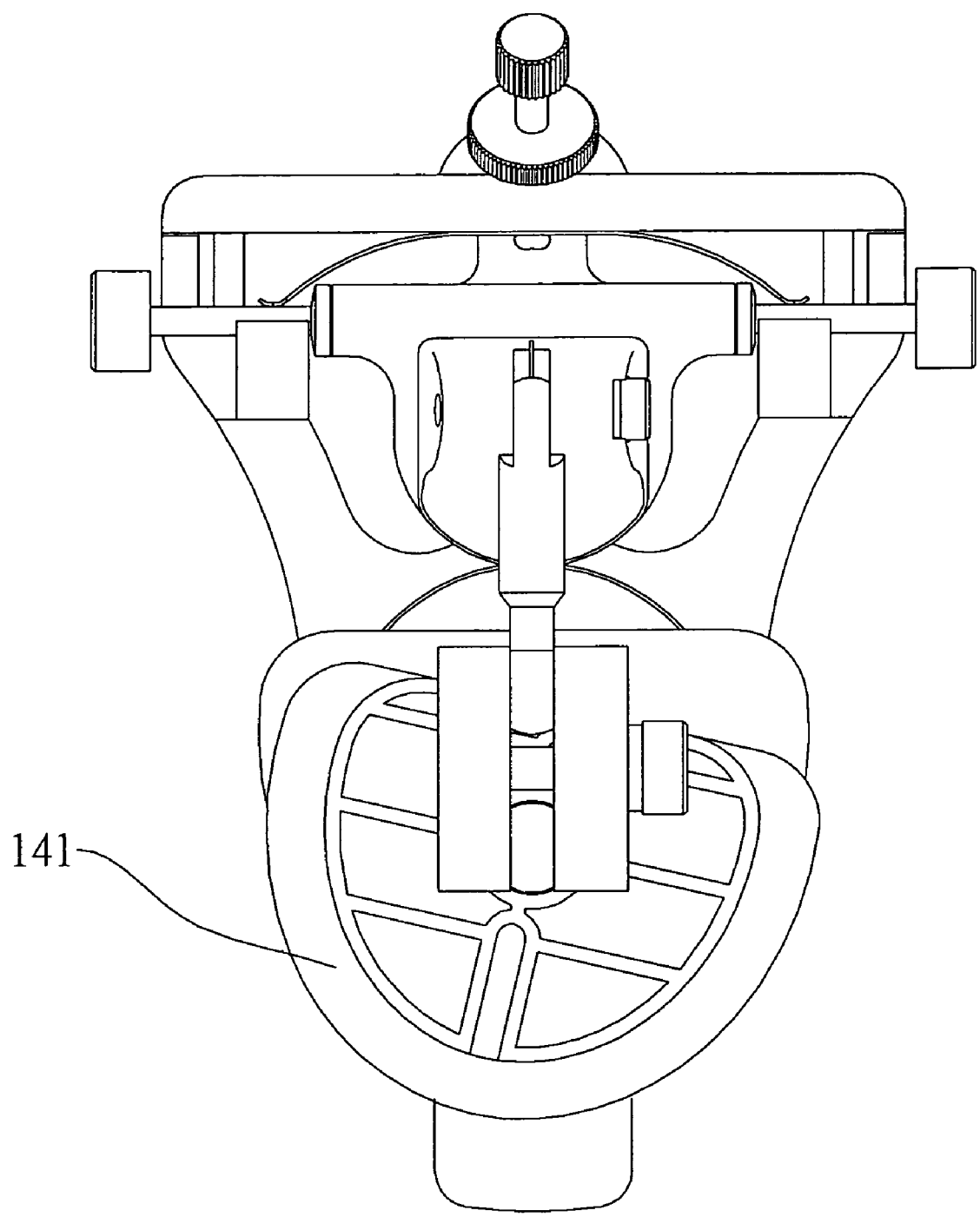

Referring to FIG. 4, the universal connector 143 will cause that the upper teeth mold T moves toward the direction indicated by the arrow H, as illustrated in FIG. 5. Or as illustrated in FIGS. 6 and 7, as illustrated by the arrow V, the first positioning block 141 passes through the universal connector 143 to move three-directionally. Of course, the upper teeth mold T can lift or descend proportionally.

In summary, in the present invention, by the universal connector 143, the upper teeth mold T can move three directionally and can lift or descend proportionally so as to avoid the error in manufacturing of the teeth mold. Thus the teeth mold T can be made precisely and the condition of the teeth mold T can be viewed conveniently. Furthermore, the teeth mold T can be sent directly without needing to send the teeth frame 10. Thus, the manufacturer can make the teeth mold T continuously without affecting the working time.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A tooth mold retaining frame comprising:

an L shape seat (10); two lateral sides of the L shape seat (10) being extended from a button seat; and a supporting frame (12) being installed above the two lateral sides; each of two ends of the supporting frame (12) having a retaining groove;

pivotal block (142) having a pivotal rod (142A) and a connecting portion; two ends of the pivotal rod (142A) being secured to the two retaining grooves of the supporting frame;

a universal connector (143); one end of the universal connector (143) being connected to the connecting portion of the pivotal block (142);

a first positioning block (141); a lower side of the first positioning block (141) having a protrusion (16) and at least one nose; the first positioning block (141) being connected to the universal connector (143); the first positioning block (141) being movable with respect to the universal connector (143);

a second positioning block (13) being positioned on the lower seat (17) and having a protrusion (16) and at least one nose; and a first fine adjust unit (20) including a top plate (21) and an adjust button (22); the top plate (21) being connected to the pivotal block (142); the adjust button (22) passing through the supporting frame (12) and one end thereof resisting against the top plate (21) so that the top plate (21) moves longitudinally to drive the pivotal block (142), universal connector (143) and the first positioning block (141);

a fine-adjust device (40) installed on the L shape seat (10) by using an adjust screw (143F) to adjust the second positioning block (13) to move leftwards or rightwards; and a second positioning block (13) including a telescopic rod (31) one end of which is installed to the L shape seat (10) and another end of which resists against the pivotal block; the telescopic rod (31) having an adjust button for adjusting a length of the telescopic rod (31) so as to adjust the position of seat; wherein by using the first fine adjust unit, second fine adjust unit and the fine-adjust device, an upper teeth mold, and a lower teeth mold can move with respect to one another precisely.

2. The tooth mold retaining frame as claimed in claim 1, wherein the universal connector (143) including a first rod body (143B) and a first ball valve (143A) connected at an upper end of the first rod body (143B); the first ball valve (143A) is pivoted to the connecting portion of the pivotal block (142) so that the first rod body and the pivotal block (142) are formed as a movably joint.

3. The tooth mold retaining frame as claimed in claim 2, wherein the universal connector (143) further includes a second rod body (143D) and a second ball valve (143C); one end of the second rod body is connected to the second ball valve (143C); the second ball valve (143C) is connected to the first positioning block (141) so that the first positioning block (141) and the universal connector (143) are movable with respect to the pivotal block (142) and are lifted.

4. The tooth mold retaining frame as claimed in claim 3, wherein universal connector (143) further includes a clamping unit which includes two clamping blocks (143E) and one adjust screw (143F); the adjust screw (143F) passes through the two clamping blocks (143E) so as to tighten or release the two clamping block (143E) and each clamping block (143)E is formed with two recesses (143G) at a side facing to another clamping block (143E) for receiving the first ball valve and the second ball valve (143C).

5. The tooth mold retaining frame as claimed in claim 1, wherein each of the first positioning block (141) and second positioning block (13) has three noses.

6. The tooth mold retaining frame as claimed in claim 1, wherein each nose has a tapered shape.

7. The tooth mold retaining frame as claimed in claim 1, wherein each of the protrusions of the first positioning block (141) and second positioning block (13) is installed wit a magnet.

* * * * *